US010143511B2

(12) United States Patent
Yasunaga

(10) Patent No.: US 10,143,511 B2
(45) Date of Patent: Dec. 4, 2018

(54) THERAPEUTIC TREATMENT DEVICE

(71) Applicant: OLYMPUS CORPORATION, Tokyo (JP)

(72) Inventor: Shinji Yasunaga, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 55 days.

(21) Appl. No.: 14/751,447

(22) Filed: Jun. 26, 2015

(65) Prior Publication Data

US 2015/0289922 A1 Oct. 15, 2015

Related U.S. Application Data

(63) Continuation of application No. PCT/JP2013/074951, filed on Sep. 13, 2013.

(30) Foreign Application Priority Data

Dec. 27, 2012 (JP) ................. 2012-285557

(51) Int. Cl.
*A61B 18/08* (2006.01)
*A61B 18/14* (2006.01)
(Continued)

(52) U.S. Cl.
CPC ........ *A61B 18/085* (2013.01); *A61B 18/1445* (2013.01); *H05B 3/26* (2013.01);
(Continued)

(58) Field of Classification Search
CPC .............. A61B 18/085; A61B 18/1445; A61B 2018/00101; A61B 2018/00095; A61B 2018/00178
See application file for complete search history.

(56) References Cited

U.S. PATENT DOCUMENTS 4,976,711 A * 12/1990 Parins ................ A61B 18/1492
606/48
5,151,102 A * 9/1992 Kamiyama ........ A61B 18/1442
606/45
(Continued)

FOREIGN PATENT DOCUMENTS

JP 200540408 A 2/2005
JP 2005348820 A 12/2005
(Continued)

OTHER PUBLICATIONS

Extended Supplementary European Search Report dated Aug. 2, 2016 in related European Application No. 13 86 7810.7.
(Continued)

*Primary Examiner* — Linda Dvorak
*Assistant Examiner* — Ryan T Clark
(74) *Attorney, Agent, or Firm* — Scully, Scott, Murphy & Presser, P.C.

(57) ABSTRACT

A living tissue to be treated is brought into contact with a first high-frequency electrode having high thermal conductivity. A substrate on which an electric resistance pattern is formed is longer than the first electrode. The substrate includes an end portion projected from the first high-frequency electrode. A first lead connection portion electrically connected to the electric resistance pattern is formed on the projected end portion. The substrate is pasted to the first electrode by use of a high-thermal-conductivity heat-resistant adhesive sheet. A lead line for applying power to the electric resistance pattern is arranged in the first lead connection portion where it extends in the longitudinal direction of the first electrode and on the side close to the first electrode.

5 Claims, 14 Drawing Sheets

(51) Int. Cl.
*H05B 3/26* (2006.01)
*A61B 18/00* (2006.01)
*A61B 17/00* (2006.01)
(52) U.S. Cl.
CPC ............... *A61B 2017/0023* (2013.01); *A61B 2017/00477* (2013.01); *A61B 2017/00526* (2013.01); *A61B 2017/00973* (2013.01); *A61B 2018/00083* (2013.01); *A61B 2018/00095* (2013.01); *A61B 2018/00178* (2013.01); *A61B 2018/00589* (2013.01); *A61B 2018/00595* (2013.01); *A61B 2018/00607* (2013.01); *A61B 2018/00916* (2013.01); *A61B 2018/00988* (2013.01); *F04C 2270/041* (2013.01); *H05B 2203/003* (2013.01); *H05B 2203/017* (2013.01)

(56) References Cited

U.S. PATENT DOCUMENTS

| | | | |
|---|---|---|---|
| 5,179,956 A * | 1/1993 | Harada | A61B 5/02233 600/485 |
| 7,145,113 B2 | 12/2006 | Aoki | |
| 2003/0060816 A1* | 3/2003 | Lida Koji | A61B 18/085 606/29 |
| 2003/0073987 A1* | 4/2003 | Sakurai | A61B 17/320068 606/28 |
| 2003/0144652 A1 | 7/2003 | Baker et al. | |
| 2003/0187429 A1* | 10/2003 | Karasawa | A61B 18/085 606/28 |
| 2004/0092923 A1* | 5/2004 | Miura | A61B 18/085 606/28 |
| 2005/0021017 A1* | 1/2005 | Karasawa | A61B 18/085 606/28 |
| 2005/0033136 A1* | 2/2005 | Govari | A61B 5/0422 600/374 |
| 2005/0159745 A1* | 7/2005 | Truckai | A61B 18/1442 606/51 |
| 2005/0222560 A1* | 10/2005 | Kimura | A61B 18/085 606/28 |
| 2005/0288747 A1 | 12/2005 | Aoki et al. | |
| 2006/0217706 A1* | 9/2006 | Lau | A61B 17/29 606/45 |
| 2007/0016053 A1* | 1/2007 | Lo | A61B 5/02438 600/459 |
| 2007/0078452 A1* | 4/2007 | Sekino | A61B 17/29 606/27 |
| 2007/0260233 A1* | 11/2007 | Miura | A61B 18/08 606/27 |
| 2008/0015567 A1* | 1/2008 | Kimura | A61B 18/1442 606/41 |
| 2009/0112200 A1 | 4/2009 | Eggers | |
| 2009/0198224 A1 | 8/2009 | McGaffigan | |
| 2010/0185196 A1 | 7/2010 | Sakao et al. | |
| 2011/0077629 A1* | 3/2011 | Tanaka | A61B 18/085 606/28 |
| 2011/0270250 A1* | 11/2011 | Horner | A61B 18/085 606/49 |
| 2013/0018372 A1* | 1/2013 | Sims | A61B 17/285 606/45 |
| 2014/0074087 A1 | 3/2014 | Yasunaga | |

FOREIGN PATENT DOCUMENTS

| | | |
|---|---|---|
| JP | 2006305236 A | 11/2006 |
| JP | 2011218182 A | 11/2011 |
| WO | 2008/051411 A2 | 5/2008 |
| WO | 2012/161163 A1 | 11/2012 |

OTHER PUBLICATIONS

Chinese Office Action dated Aug. 30, 2016 in Chinese Patent Application No. 201380068384.4.
English translation of International Preliminary Report on Patentability dated Jul. 9, 2015 together with the Written Opinion received in related International Application No. PCT/JP2013/074951.
Japanese Office Action dated Apr. 21, 2015 received in Patent Application No. 2015-003537 together with an English translation.
International Search Report dated Nov. 12, 2013 received in International Application No. PCT/JP2013/074951.
Office Action dated Mar. 22, 2018 received in U.S. Appl. No. 15/493,399.
Extended Supplementary European Search Report dated Jun. 12, 2018 in European Patent Application No. 18 15 5737.2.

* cited by examiner

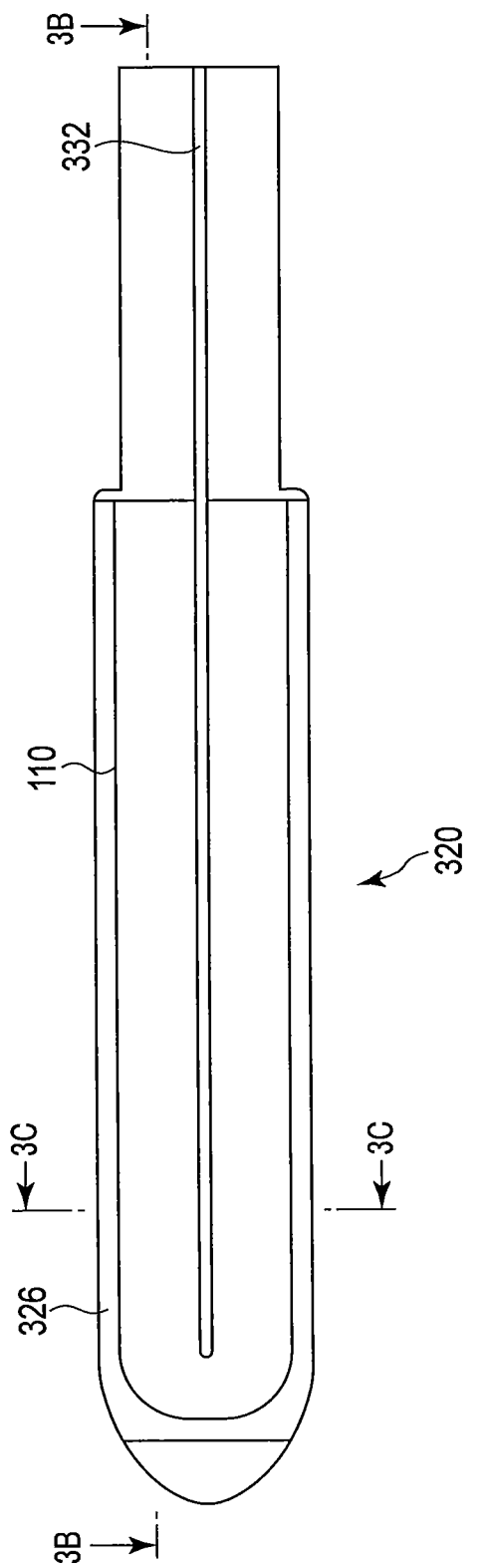
F I G. 3A

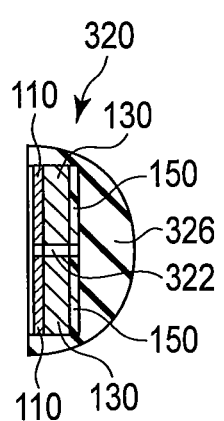
F I G. 3C

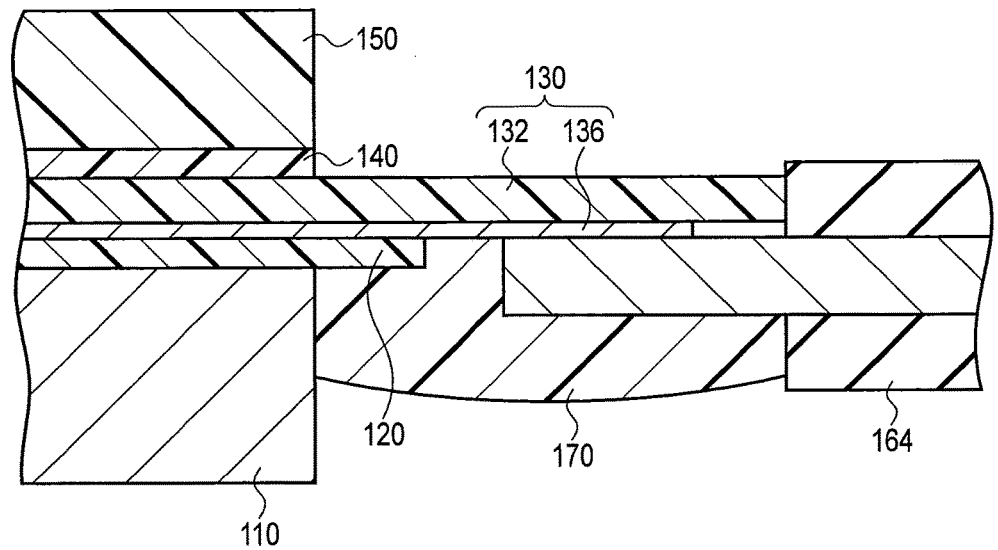
F I G. 12
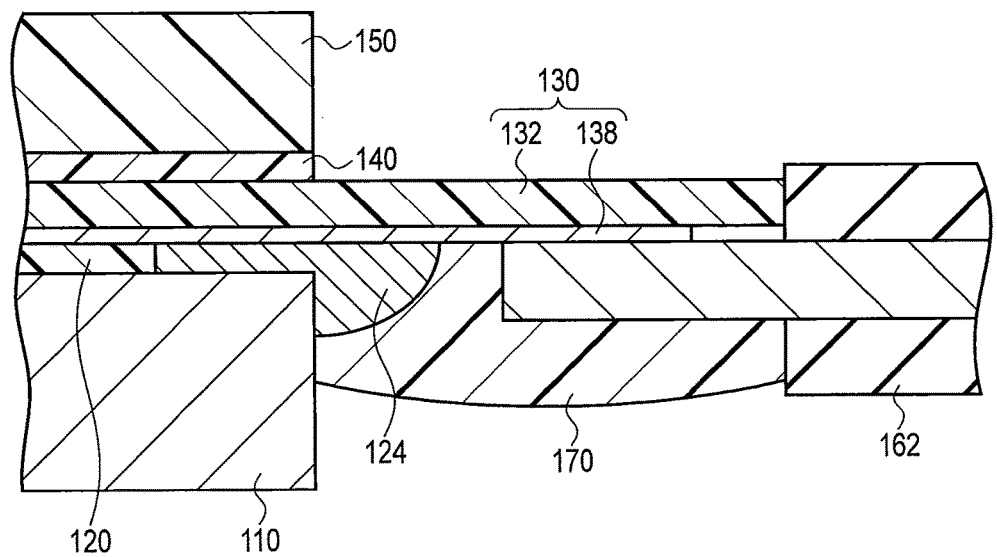
F I G. 13

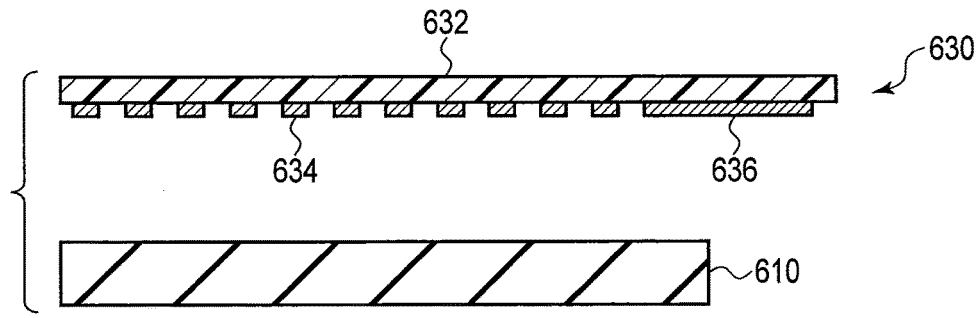
F I G. 14A
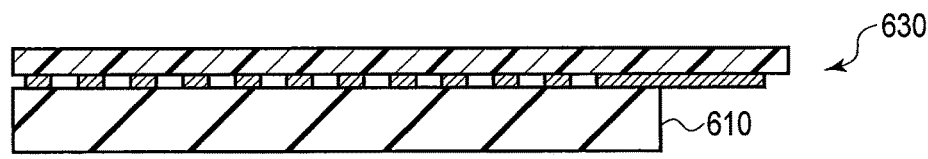
F I G. 14B
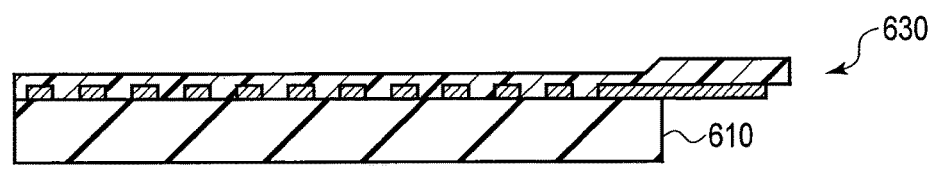
F I G. 14C
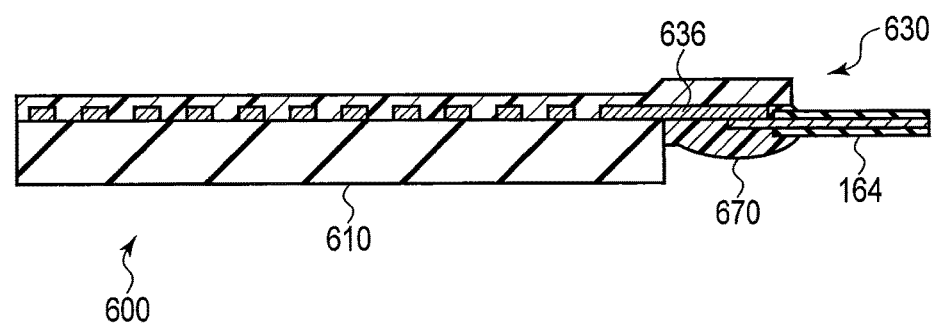
F I G. 14D

THERAPEUTIC TREATMENT DEVICE

CROSS-REFERENCE TO RELATED APPLICATIONS

This application is a Continuation Application of PCT Application No. PCT/JP2013/074951, filed Sep. 13, 2013 and based upon and claiming the benefit of priority from prior Japanese Patent Application No. 2012-285557, filed Dec. 27, 2012, the entire contents of all of which are incorporated herein by reference.

BACKGROUND OF THE INVENTION

1. Field of the Invention

The present invention relates to a therapeutic treatment device.

2. Description of the Related Art

A therapeutic treatment device which treats a living tissue using thermal energy is generally known in the art. For example, Jpn. Pat. Appln. KOKAI Publication No. 2006-305236 discloses the following therapeutic treatment device. In the therapeutic treatment device, a substrate having a heat generating element thereon is made of a metallic member having excellent thermal conductivity. A heat generating section having a thin film resistor is formed on the substrate. A lead line for applying power is provided on the heat generating section. A filler is provided at the joint between the heating generating section and the lead line, for ensuring electric insulation. In order to ensure reliable temperature control property even when a living tissue is partly contacts the heat generating device, the substrate of the heat generating element must have high thermal conductivity. For this reason, the substrate is made of a thick member having high thermal conductivity.

BRIEF SUMMARY OF THE INVENTION

According to an aspect of the invention, a therapeutic treatment device for treating a living tissue by heating includes a heat conduction plate comprising a first major surface and a second major surface opposite to each other and configured to apply heat to the living tissue, with the first major surface kept in contact with the living tissue; a substrate provided on the second major surface of the heat conduction plate and comprising a projected portion projected from the heat conduction plate; an electric resistance pattern formed on the substrate, thermally coupled to the heat conduction plate and configured to generate heat upon application of a voltage; a first lead connection portion formed on the projected portion of the substrate and electrically connected to the electric resistance pattern; and a first lead line arranged closer to the heat conduction plate than is the substrate, electrically connected to the first lead connection portion, and configured to apply power to the electric resistance pattern.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3A is a schematic plan view showing an example of a first holding member applicable to each embodiment.

FIG. 3C is a cross section taken along line 3C-3C shown in FIG. 3A.

FIG. 12 is a sectional view showing how a first lead connection portion and a first-heater current supply line are in the first electrode section of the first embodiment.

FIG. 13 is a sectional view showing how a second lead connection portion and a first-high-frequency-electrode current supply line are in the first electrode section of the first embodiment.

FIG. 14A is an explanatory view showing an example of a heat transfer member and an example of a manufacturing method according to a second embodiment.

FIG. 14B is an explanatory view showing an example of a heat transfer member and an example of a manufacturing method according to the second embodiment.

FIG. 14C is an explanatory view showing an example of a heat transfer member and an example of a manufacturing method according to the second embodiment.

FIG. 14D is an explanatory view showing an example of a heat transfer member and an example of a manufacturing method according to the second embodiment.

DETAILED DESCRIPTION OF THE INVENTION

First Embodiment

Figure 1:
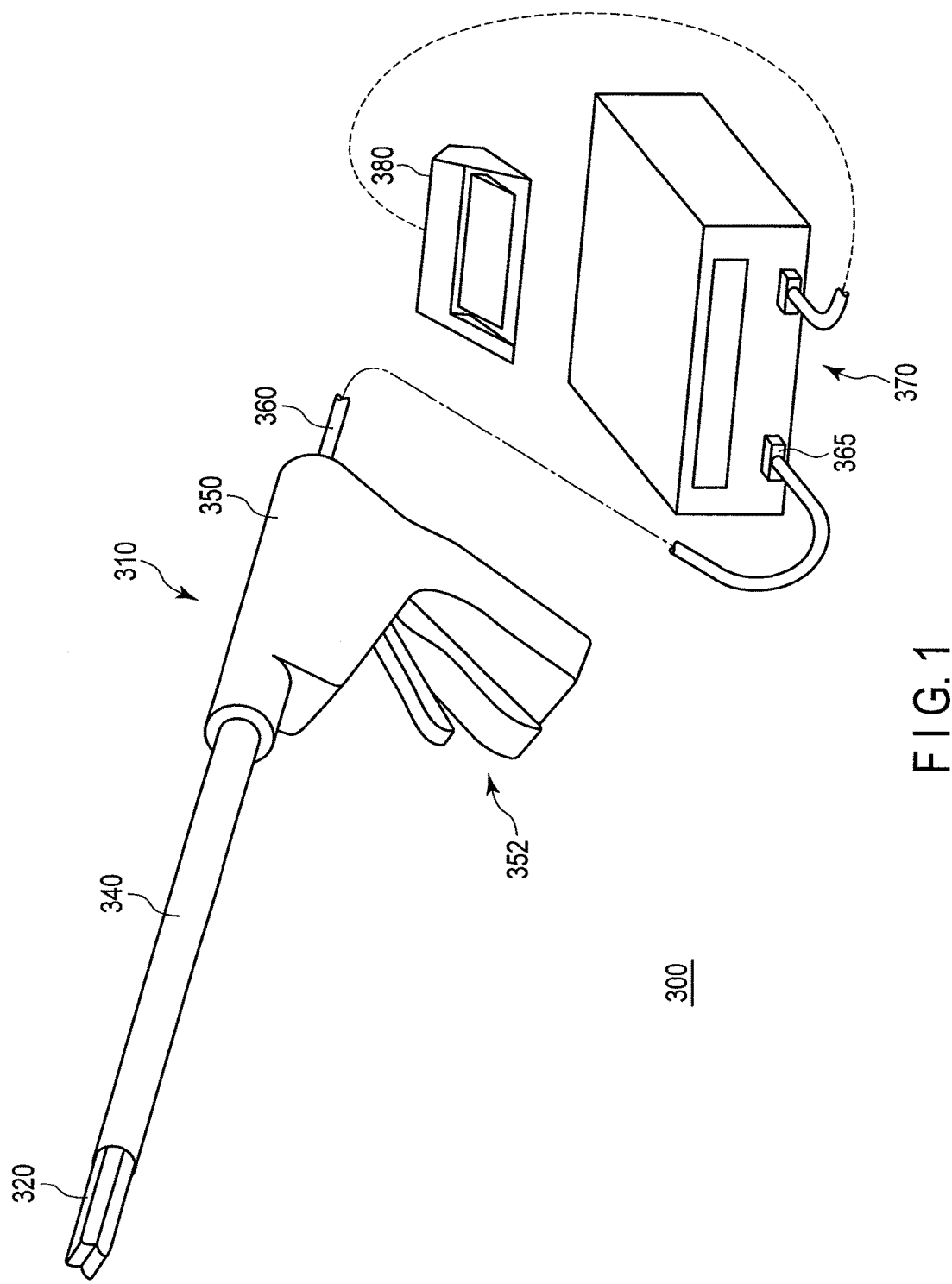
FIG. 1 is a perspective view showing an example of a therapeutic treatment system applicable to each embodiment.

A description will now be given of the first embodiment of the present invention with reference to the accompanying drawings. The therapeutic treatment device of the embodiment is used for treating a living tissue. The therapeutic treatment device applies high-frequency energy and thermal energy to the living tissue. FIG. 1 broadly shows how the therapeutic treatment tool 300 looks like. As shown in FIG. 1, the therapeutic treatment tool 300 comprises an energy treatment tool 310, a control device 370 and a footswitch 380.

The energy treatment tool 310 is a linear type surgical treatment tool which is penetrated through an abdominal wall when used. The energy treatment tool 310 comprises a handle 350, a shaft 340 attached to the handle 350, and a holding section 320 at the distal end of the shaft 340. The holding section 320 can be opened/closed and holds the living tissue to be treated when the living tissue is coagulated or incised. In the descriptions set forth below, the portion closer to the holding section 320 will be referred to as the "distal end", and the portion closer to the handle 350 will be referred to as the "proximal end." The handle 350 comprises a plurality of operation knobs 352 for operating the holding section 320. The handle 350 is provided with a nonvolatile memory (not shown) for storing characteristic values of the energy treatment tool 310. Needless to say, the shape of the energy treatment tool 310 depicted in FIG. 1 is merely an example, and the energy treatment tool 310 may be configured to have any other shape as long as it has a similar function. For example, the energy treatment tool 310 may be in the shape of forceps, or the shaft may be curved.

The handle 350 is connected to the control device 370 through a cable 360. The cable 360 and the control device 370 are connected by a connector 365, and the connector 365 is detachable. In other words, the therapeutic treatment tool 300 is configured to disposably use an energy treatment tool 310. The footswitch 380 is connected to the control device 370. The footswitch 380 operated by foot may be replaced with a manually operatable switch or any other type of switch. The energy supply to the energy treatment tool 310 from the control device 370 is switched on or off by operating the pedal of the footswitch 380 by the operator.

Figure 2A:
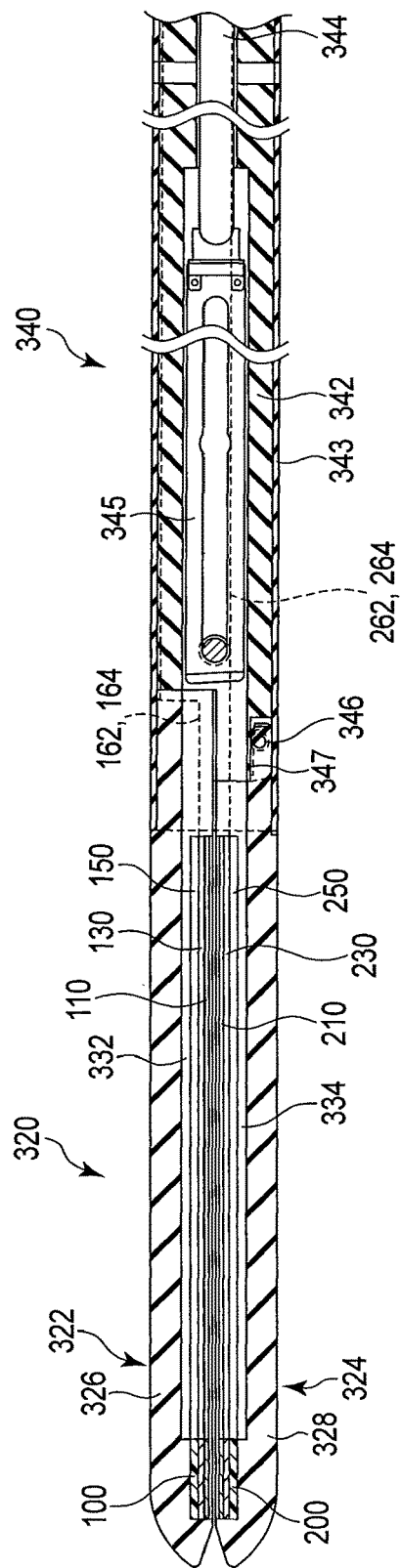
FIG. 2A is a schematic sectional view showing examples of a shaft and a holding section of an energy treatment tool applicable to each embodiment, the holding section being depicted as being closed.
Figure 2B:
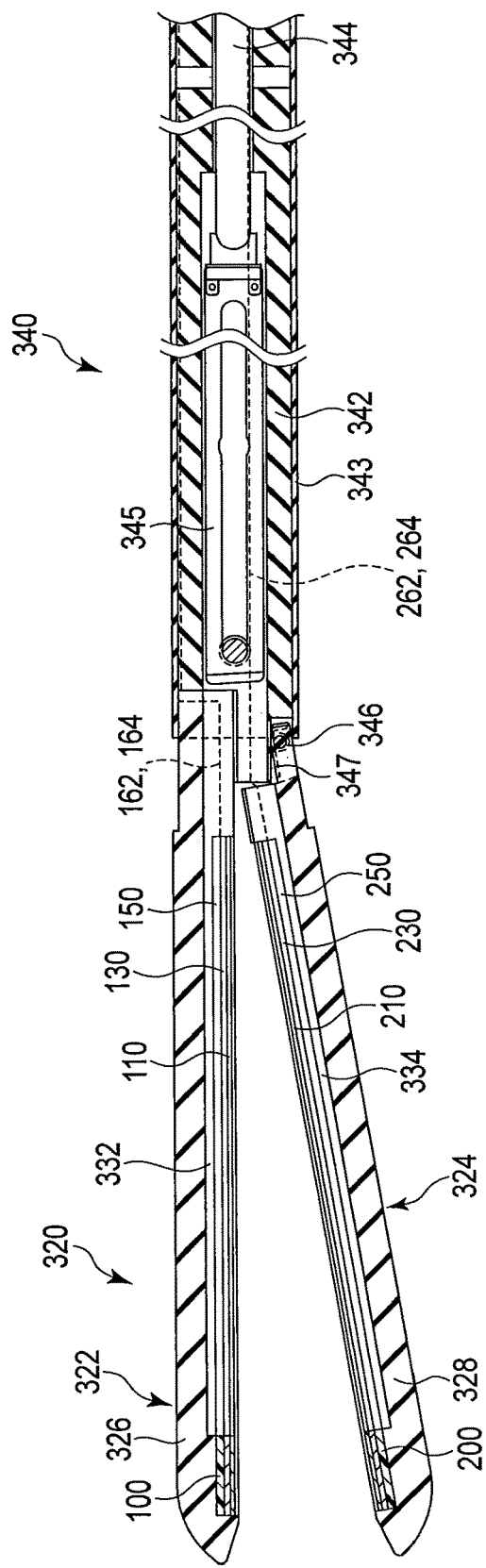
FIG. 2B is a schematic sectional view showing examples of the shaft and the holding section of the energy treatment tool applicable to each embodiment, the holding section being depicted as being open.

An example of the holding section 320 and shaft 340 is shown in FIGS. 2A and 2B. FIG. 2A depicts the holding section 320 in the closed state, while FIG. 2B depicts the holding section 320 in the open state. The shaft 340 comprises a tubular member 342 and a sheath 343. The tubular member 342 is fixed to the handle 350 at the proximal end thereof. The sheath 343 is located on the outer side of the tubular member 342 and slidable in the axial direction of the tubular member 342.

The holding section 320 is located at the distal end of the tubular member 342. The holding section 320 comprises a first holding member 322 and a second holding member 324. The proximal portion of the first holding member 322 is fixed to the distal end portion of the tubular member 342 of the shaft 340. The proximal portion of the second holding member 324 is rotatably supported by the distal end portion of the tubular member 342 by means of a support pin 346. The second holding member 324 is rotatable around the axis of the support pin 346, and opens or closes with respect to the first holding member 322.

In the closed state of the holding section 320, a cross section of the combination of the proximal portion of the first holding member 322 and the proximal portion of the second holding member 324 is circular. The second holding member 324 is urged by an elastic member 347 (e.g., a leaf spring) in such a direction as to open with respect to the first holding member 322. When the sheath 343 is slid toward the distal end relative to the tubular member 342, and the proximal portion of the first holding member 322 and the proximal portion of the second holding member 324 are covered by the sheath 343, the first holding member 322 and the second holding member 324 are set in the closed state against the urging force of the elastic member 347, as shown in FIG. 2A. On the other hand, when the sheath 343 is slid toward the proximal end of the tubular member 342, the second holding member 324 opens with respect to the first holding member 322 by the urging force of the elastic member 347, as shown in FIG. 2B.

A first-high-frequency-electrode current supply line 162 and a second-high-frequency-electrode current supply line 262 are inserted through the tubular member 342. The first-high-frequency-electrode current supply line 162 and the second-high-frequency-electrode current supply line 262 are respectively connected to a first high-frequency electrode 110 and a second high-frequency electrode 210, which will be mentioned below. A pair of first-heater current supply lines 164 and a pair of second-heater current supply lines 264 are also inserted through the tubular member 342. The first-heater current supply lines 164 are connected to an electrothermal conversion element 130, which is a heat generating member arranged in a first high-frequency electrode 110 (described below), while the second-heater current supply lines 264 are connected to an electrothermal conversion element 230, which is a heat generating member arranged in a second high-frequency electrode 210.

A driving rod 344, connected to one of the operation knobs 352 at the proximal end, is located inside the tubular member 342. The driving rod 344 is movable in the axial direction of the tubular member 342. A cutter 345 in the form of thin plate having an edge at the distal end is attached to the distal end of the driving rod 344. When the operation knob 352 is operated, the driving rod 344 moves the cutter 345 in the axial direction of the tubular member 342. When the cutter 345 is moved to the distal end, it is received in a first cutter guide groove 332 and a second cutter guide groove 334, both formed in the holding section 320.

Figure 3B:
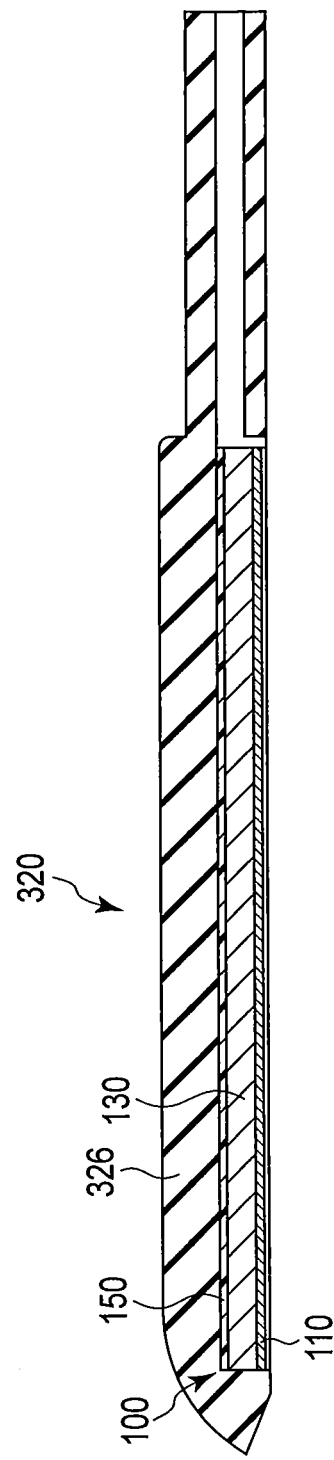
FIG. 3B is a longitudinal section taken along line 3B-3B shown in FIG. 3A.

The first holding member 322 is schematically shown in FIGS. 3A to 3C. As shown in these Figures, a first cutter guide groove 332 for guiding the cutter 345 described above is formed in the first holding member 322. A first high-frequency electrode 110 made of e.g. a copper thin plate is provided on the first holding member 322. The first high-frequency electrode 110 is configured such that its one major surface comes into contact with a living tissue (that major surface will be hereinafter referred to as the first major surface). Since the first high-frequency electrode 110 is provided with the first cutter guide groove 332, its planar shape is in the form of "U", as shown in FIG. 3A. As will be described in detail, the first-high-frequency-electrode current supply line 162 is electrically connected to the first high-frequency electrode 110. The first high-frequency electrode 110 is connected to the control device 370 by way of the first-high-frequency-electrode current supply line 162 and the cable 360. As will be described below, an electrothermal conversion element 130 and a cover member 150 are arranged on the second major surface of the first high-frequency electrode 110, which is a surface that does not come into contact with a living tissue. In this manner, a first electrode section 100, provided with the first high-frequency electrode 110, the electrothermal conversion element 130, the cover member 150, etc., is fabricated. The first electrode section 100 is embedded in the first holding member 326 and secured therein. Details of the example of the first electrode section 100 will be described later.

As shown in FIGS. 2A and 2B, the second holding member 324 has a shape symmetric to that of the first holding member 322 and has a similar structure to that of the first holding member 322. The second holding member 324 has a second cutter guide groove 334 at the position corresponding to the position of the first cutter guide groove 332. The second holding member 324 comprises a second high-frequency electrode 210 at the position corresponding to that of the first high-frequency electrode 110. The second high-frequency electrode 210 is configured such that its one major surface is brought into contact with a living tissue. The second high-frequency electrode 210 is connected to the control device 370 by way of the second-high-frequency-electrode current supply line 262 and the cable 360.

An electrothermal conversion element 230 and a cover member 250 are arranged on the surface of the second high-frequency electrode 210 that is not brought into contact with a living tissue. In this manner, a second electrode section 200, provided with the second high-frequency electrode 210, electrothermal conversion element 230, cover member 250, etc., is fabricated. The second electrode section 200 is embedded in the second holding member 328 and secured therein.

Figure 4:
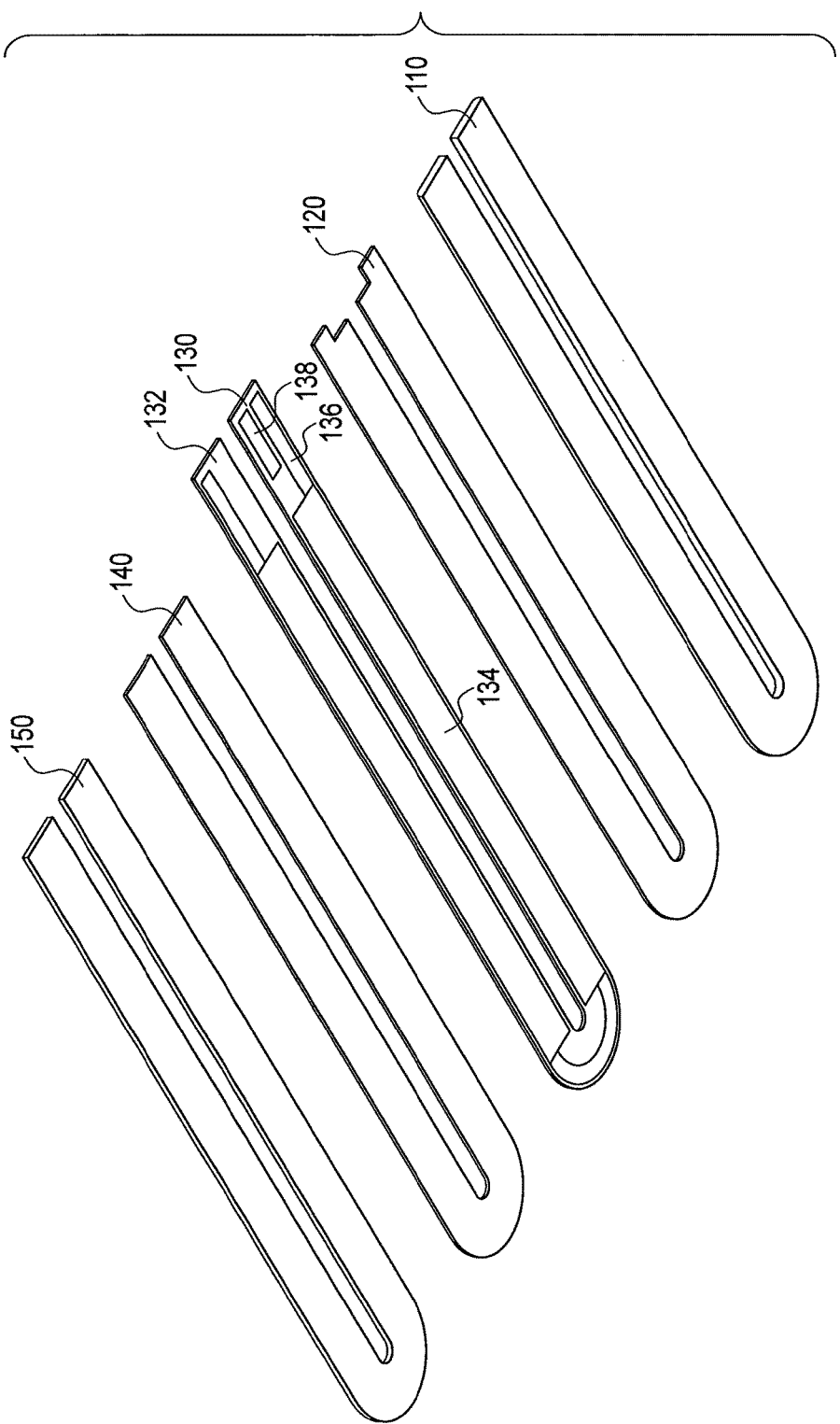
FIG. 4 is an exploded perspective view showing a first electrode section according to a first embodiment.

A detailed description will be given of the first electrode section 100. Since the second electrode section 200 has a similar structure to that of the first electrode section 100, a description of the second electrode section 200 will be omitted. An exploded perspective view of the first electrode section 100 is shown in FIG. 4. As shown in this Figure, the first electrode section 100 comprises a first high-frequency electrode 110, a high-thermal-conductivity heat-resistant adhesive sheet 120, an electrothermal conversion element 130, a heat-resistant adhesive sheet 140 and a cover member 150. The first high-frequency electrode 110, high-thermal-conductivity heat-resistant adhesive sheet 120, electrothermal conversion element 130, heat-resistant adhesive sheet 140 and cover member 150 have a "U" shape. The first high-frequency electrode 110 is made of copper, for example, and has a thickness of about 0.5 mm, for example.

Figure 5:
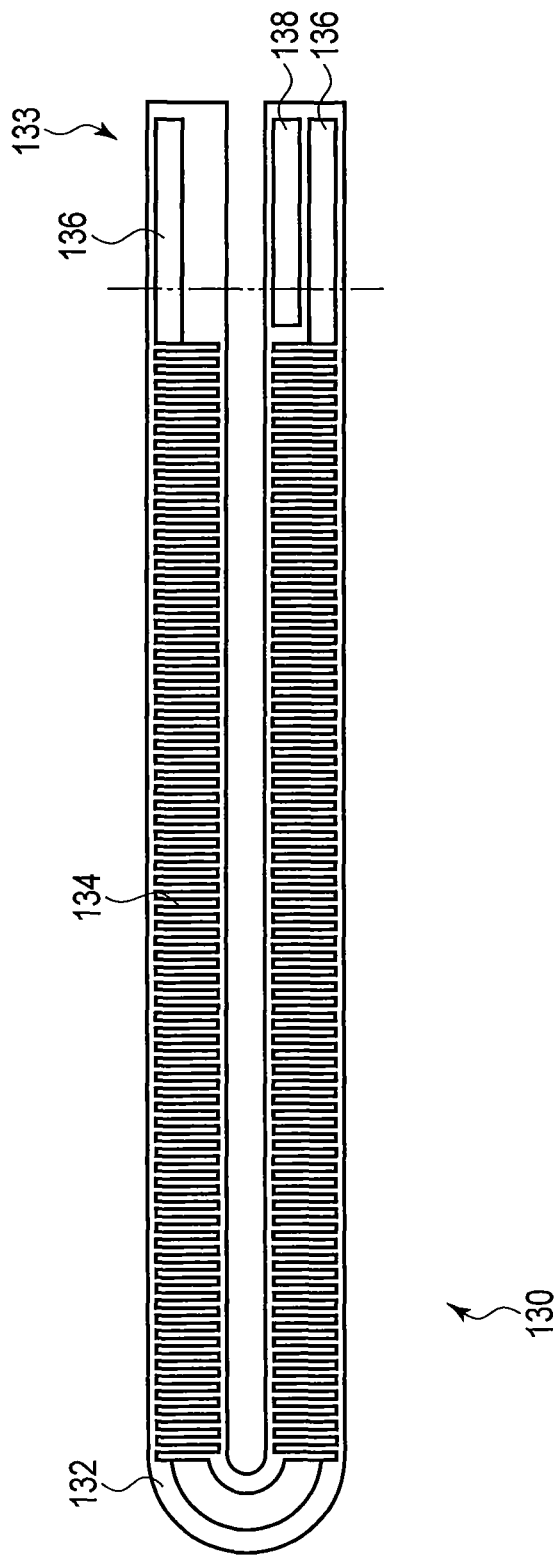
FIG. 5 is a plan view showing an example of an electrothermal conversion element according to the first embodiment.

A plan view of the electrothermal conversion element 130 is shown in FIG. 5. As shown in this Figure, the electrothermal conversion element 130 includes a polyimide substrate 132, for example. The substrate 132 has a distal end portion similar in shape to that of the first high-frequency electrode 110, and is slightly longer than the first high-frequency electrode 110. In FIG. 5, the position corresponding to the proximal end of the first high-frequency electrode 110 when the first electrode section 100 is fabricated is indicated by the two-dot-dash line. The portion projected from the first high-frequency electrode 110 will be referred to as a projected portion 133.

An electric resistance pattern 134, e.g., a pattern of stainless steel (SUS), is formed on the substrate 132, except on the projected portion 133. A pair of first lead connection portions 136, connected to the respective ends of the electric resistance pattern 134, is formed as SUS patterns on the end portions of the substrate 132, including the projected portion 133. The electric resistance pattern 134 generates heat when a voltage is applied between the first lead connection portions 136. As can be seen from this, the electrothermal conversion element 130 functions as a sheet heater.

A second lead connection portion 138, insulated from the electric resistance pattern 134 and the first lead connection portions 136, is formed as SUS patterns on the end portions of the substrate 132 including the projected portion 133. The second lead connection portion 138 is connection portion to which the first-high-frequency-electrode current supply line 162 for applying voltage to the first high-frequency electrode 110 is connected. The second lead connection portion 138 has its distal end portions located at the positions corresponding to that of the first high-frequency electrode 110. The second lead connection portion 138 need not be provided on the respective projected portions 133. Only one second lead connection portion 138 provided on one of the projected portions 133 suffices. However, two second lead connection portions 138 may be provided on the two projected portions 133. The substrate 132 has a thickness of 100 µm, for example, and the SUS patterns have a thickness of 20 µm, for example.

The first high-frequency electrode 110 and the electrothermal conversion element 130 are adhered to each other by the high-thermal-conductivity heat-resistant adhesive sheet 120. The high-thermal-conductivity heat-resistant adhesive sheet 120 is an adhesive sheet having high thermal conductivity and being heat-resistant. The high-thermal-conductivity heat-resistant adhesive sheet 120 is formed, for example, by mixing a ceramic material having high thermal conductivity, such as alumina and aluminum nitride, with epoxy resin. The high-thermal-conductivity heat-resistant adhesive sheet 120 has high adhesive property, satisfactory thermal conductivity and electric insulation property. The heat-resistant adhesive sheet has a thickness of 60 µm, for example.

Figure 6:
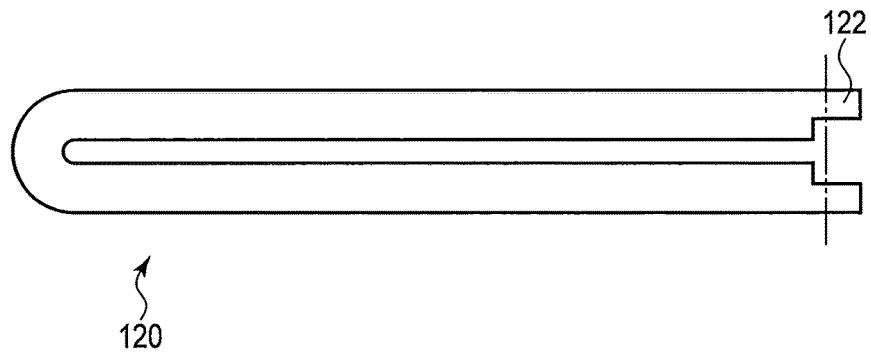
FIG. 6 is a plan view showing an example of a heat-resistant adhesive sheet having high thermal conductivity according to the first embodiment.

The shape of the high-thermal-conductivity heat-resistant adhesive sheet 120 is shown in FIG. 6. In this Figure, the position corresponding to the proximal end of the first high-frequency electrode 110 when the first electrode section 100 is fabricated is indicated by the two-dot-dash line. The high-thermal-conductivity heat-resistant adhesive sheet 120 has a shape substantially similar to that of the first high-frequency electrode 110. The high-thermal-conductivity heat-resistant adhesive sheet 120 is provided with short-circuit preventing portions 122 at the positions corresponding to the first lead connection portions 136 of the electrothermal conversion element 130. The short-circuit preventing portions 122 are more projected toward the proximal end than does the first high-frequency electrode 110. The short-circuit preventing portions 122 provide electric insulation between the first high-frequency electrode 110 and the first lead connection portions 136. The high-thermal-conductivity heat-resistant adhesive sheet 120 is shorter than the first high-frequency electrode 110 at the positions corresponding to the second lead connection portion 138. At the positions where the high-thermal-conductivity heat-resistant adhesive sheet 120 is shorter than the first high-frequency electrode 110, a conductive paste is coated, as described below, so as to provide electric connection between the first high-frequency electrode 110 and the second lead connection portion 138.

The cover member 150 is formed of a heat-resistant resin and has a thickness of about 0.3 mm, for example. The cover member 150 is pasted to the electrothermal conversion element 130 by means of the heat-resistant adhesive sheet 140. The heat-resistant adhesive sheet 140 is an adhesive sheet having high heat resistance. The heat-resistant adhesive sheet 140 is formed of an epoxy or polyimide material, for example. The heat-resistant adhesive sheet 140 has a thickness of about 50 μm, for example. The heat-resistant adhesive sheet 140 and the cover member 150 have substantially the same shape as the first high-frequency electrode 110.

In the first electrode section 100, the first high-frequency electrode 110 is thick, compared to the other members. This structure improves the thermal conductivity of the first high-frequency electrode 110, and even when a living tissue comes into partial contact with the first high-frequency electrode 110, the temperature of the first high-frequency electrode 110 is uniform. This feature is important in the temperature control performed when living tissues are inosculated or joined using the energy treatment tool 310 of the embodiment.

A description will be given of the manufacturing process of the first electrode section 100. First of all, the first high-frequency electrode 110, the high-thermal-conductivity heat-resistant adhesive sheet 120 and the electrothermal conversion element 130 are stacked on one another, and are joined by hot pressing. The electrothermal conversion element 130 is stacked, with the face having the electric resistance pattern 134 thereon being kept in contact with the first high-frequency electrode 110.

Figure 7:
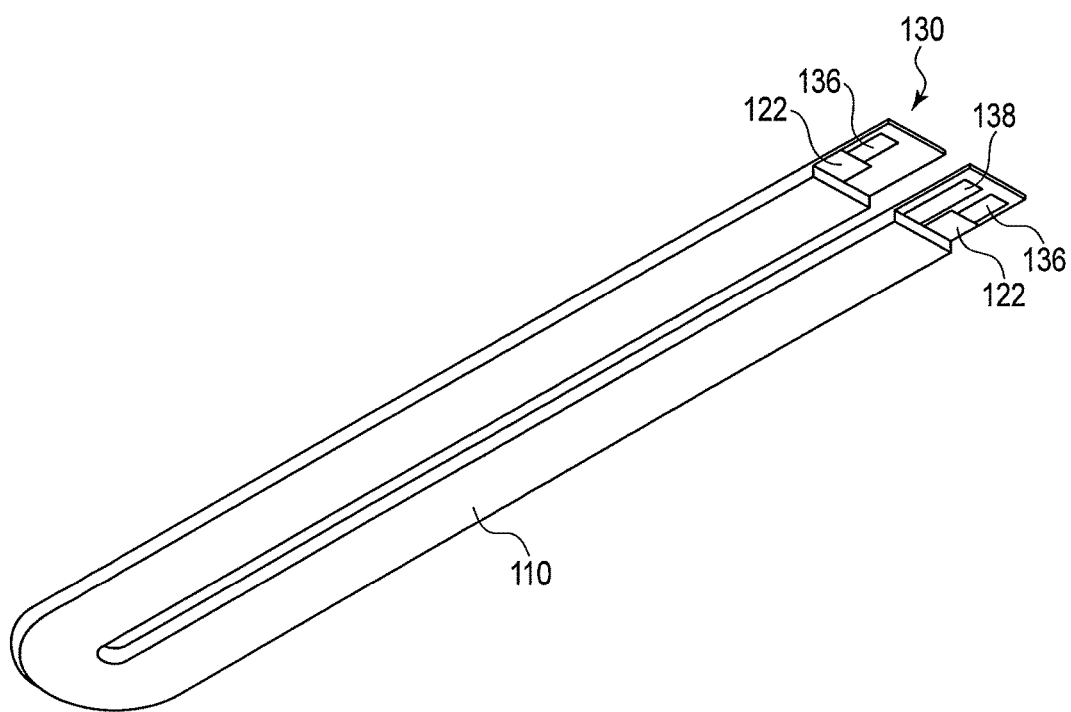
FIG. 7 is a perspective view showing an example of a state where a first high-frequency electrode and an electrothermal conversion element are joined according to the first embodiment.

A schematic view of the structure obtained after joining is shown in FIG. 7. The electric resistance pattern 134 of the electrothermal conversion element 130 is located closer to the first high-frequency electrode 110 than is the substrate 132 of the electrothermal conversion element 130, and the high-thermal-conductivity heat-resistant adhesive sheet 120 is interposed between the electric resistance pattern 134 and the first high-frequency electrode 110. As can be seen, the electric resistance pattern 134 is thermally coupled to the first high-frequency electrode 110, with the high-thermal-conductivity heat-resistant adhesive sheet 120 located therebetween. Since only the high-thermal-conductivity heat-resistant adhesive sheet 120 is present between the electric resistance pattern 134 and the first high-frequency electrode 110, the heat generated by the electric resistance pattern 134 can be transferred to the first high-frequency electrode 110 with high efficiency.

As shown in FIG. 7, the short-circuit preventing portion 122 of the high-thermal-conductivity heat-resistant adhesive sheet 120 is projected from the first high-frequency electrode 110. With this structure, the electric resistance pattern 134 of the electrothermal conversion element 130 and the first lead connection portions connected thereto are reliably insulated from the first high-frequency electrode 110. It should be noted that the high-thermal-conductivity heat-resistant adhesive sheet 120 is not present at the positions corresponding to the end portions of the second lead connection portion 138. Therefore, the second lead connection portion 138 and the first high-frequency electrode 110 can easily short-circuited to each other.

Figure 8:
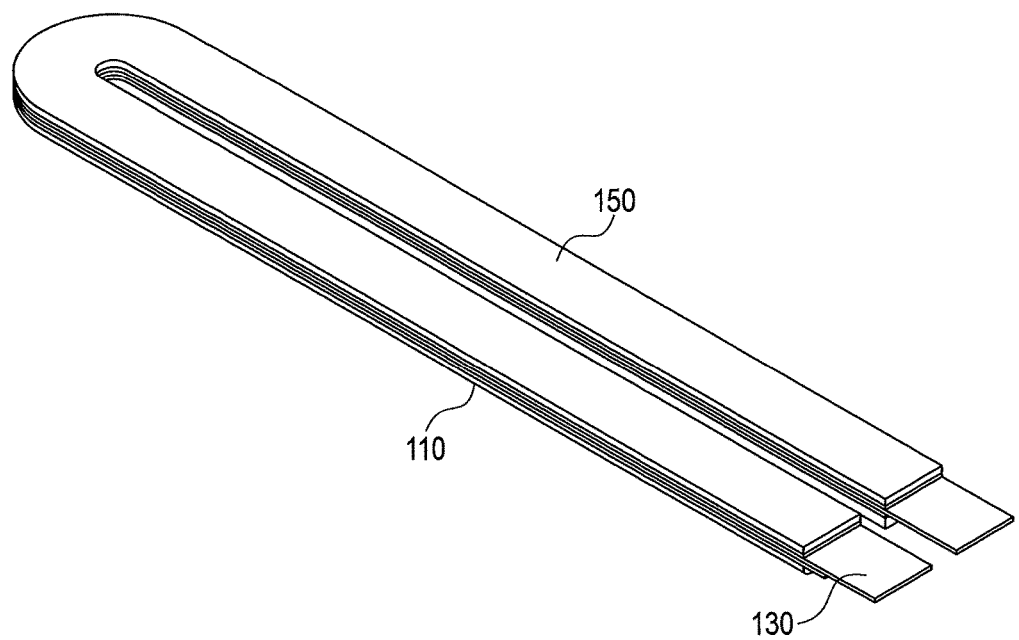
FIG. 8 is a perspective view showing an example of a state where a first high-frequency electrode, an electrothermal conversion element and a cover member are joined according to the first embodiment.

After the first high-frequency electrode 110 and the electrothermal conversion element 130 are joined, the polyimide substrate 132 of the electrothermal conversion element 130 is overlaid with the heat-resistant adhesive sheet 140 and the cover member 150, and the resultant structure is subjected to hot pressing. A perspective view of the structure submitted to hot pressing is shown in FIG. 8.

Figure 9:
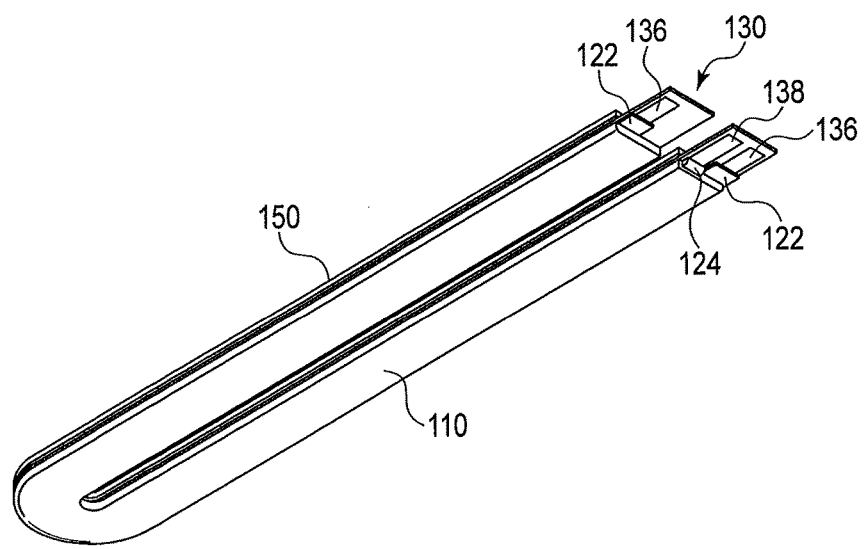
FIG. 9 is a perspective view showing an example of a state where a first electrode section of the first embodiment is coated with a conductive paste.

As shown in FIG. 9, the conductive paste 124 is formed between the second lead connection portion 138 and the first high-frequency electrode 110. As a result, the second lead connection portion 138 and the first high-frequency electrode 110 are electrically connected. As means for providing this electrical connection, welding or soldering may be used in place of the conductive paste 124.

Figure 10:
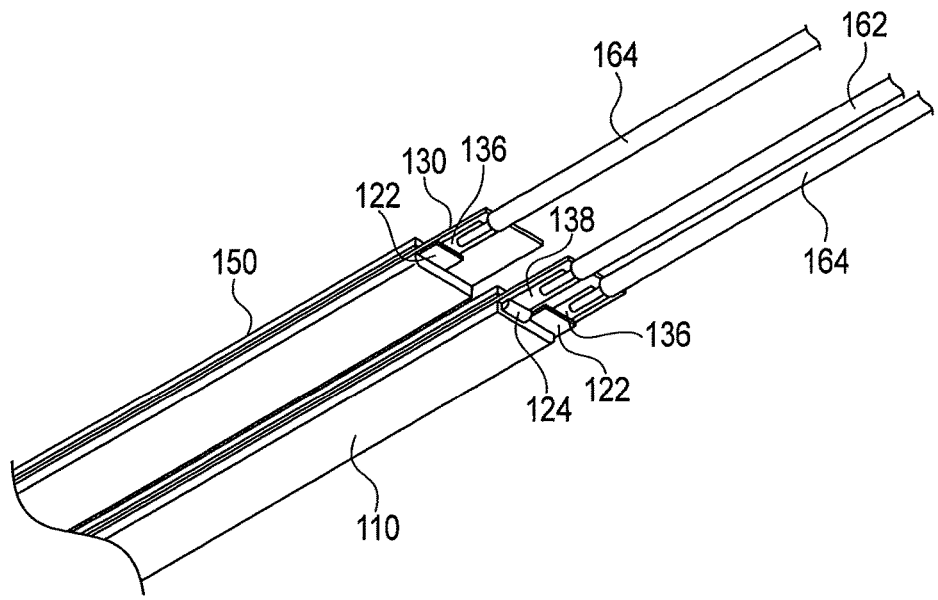
FIG. 10 is a perspective view showing an example of a state where a first-heater current supply line and a first-high-frequency-electrode current supply line are connected to a first electrode section of the first embodiment.
Figure 11:
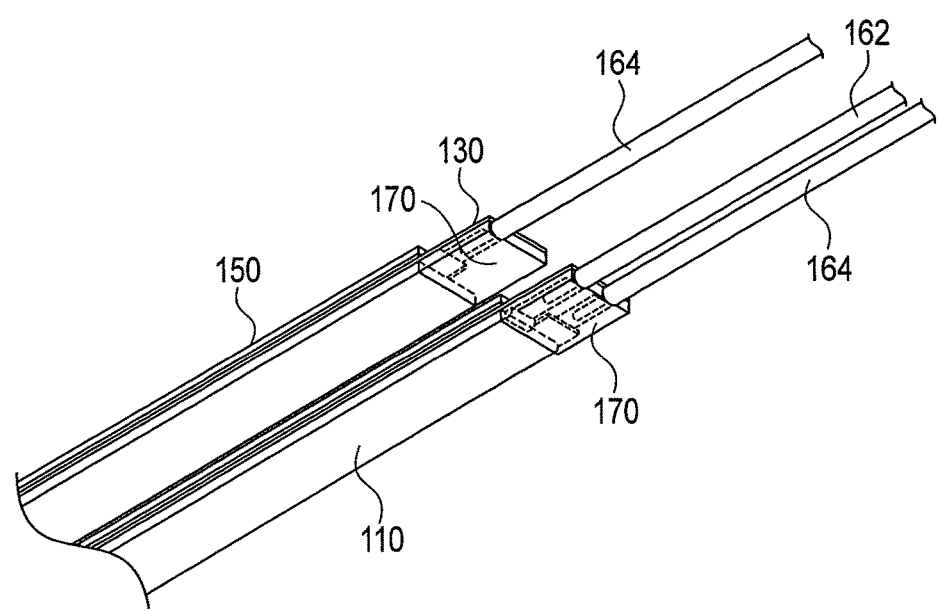
FIG. 11 is a perspective view showing an example of a state where a sealer is coated in the first electrode section of the first embodiment.

Then, the first-heater current supply lines 164 are connected to the first lead connection portions 136 for example by welding, as shown in FIG. 10. The first-high-frequency-electrode current supply line 162 is connected to the second lead connection portion 138 for example by welding. Subsequently, as shown in FIG. 11, the entire region where the connection portions of the first-high-frequency-electrode current supply line 162 and the first-heater current supply lines 164 are located are coated with the sealer 170 such as a silicone resin.

Cross sections of the proximal portion of the first electrode section 100 are shown in FIGS. 12 and 13. FIG. 12 is a cross section passing both the first-heater current supply line 164 and the first lead connection portion 136, and FIG. 13 is a cross section passing both the first-high-frequency-electrode current supply line 162 and the second lead connection portion 138. As shown in FIGS. 12 and 13, the first electrode section 100 of the embodiment is configured in such a manner that the electrothermal conversion element 130 comprising both the first lead connection portions 136 and the second lead connection portion 138 is projected from the first high-frequency electrode 110 and the cover member 150. In addition, the first lead connection portions 136 and the second lead connection portion 138 are located on that side of the substrate 132 which is closer to the first high-frequency electrode 110. It should be noted here that the first high-frequency electrode 110 is thick, compared to the other members of the first electrode section 100. As shown in FIG. 12, the first-heater current supply lines 164 are connected to the first lead connection portions 136 in such a manner as to extend from the electrothermal conversion element 130. Likewise, as shown in FIG. 13, the first-high-frequency-electrode current supply line 162 is connected to the second lead connection portion 138 in such a manner as to extend from the electrothermal conversion element 130. As can be seen from this, in the embodiment, the first-heater current supply lines 164 and the first-high-frequency-electrode current supply line 162 are not related to the thickness of the first electrode section 100. Accordingly, the first electrode section 100 can be as thin as possible.

In order to transfer the heat generated by the electrothermal conversion element 130 to the first high-frequency electrode 110, the cover member 150 should preferably have thermal conductivity lower than the thermal conductivities of the first high-frequency electrode 110 and the high-thermal-conductivity heat-resistant adhesive sheet 120. Where the cover member 150 has low thermal conductivity, the heat loss of the heat generated by the electrothermal conversion element 130 can be reduced. Although the first electrode section 100 has been described, the second electrode section 200 has a similar structure to that of the first electrode section 100 described above.

A description will now be given as to how the therapeutic treatment tool 300 operates. The operator operates the input section of the control device 370 beforehand to enter the output conditions of the therapeutic treatment tool 300, such as the setting power of a high-frequency energy output, a target temperature of a thermal energy output, and a heating time. The therapeutic treatment tool 300 can be set by individually entering the respective values or by selecting a set of setting values predetermined for each therapy.

The holding section 320 and shaft 340 of the energy treatment tool 310 are inserted, for example, into an abdominal cavity through an abdominal wall. The operator operates the operation knob 352 to open or close the holding section 320. The first holding member 322 and the second holding member 324 hold a living tissue to be treated. At the time, the living tissue to be treated comes into contact with the first major surfaces of the first high-frequency electrode 110 of the first holding member 322 and the second high-frequency electrode 210 of the second holding member 324.

After gripping the living tissue to be treated with the holding section 320, the operator operates the footswitch 380. When the footswitch 380 is turned on, high-frequency power having a predetermined value is supplied from the control device 370 to the first high-frequency electrode 110 and the second high-frequency electrode 210 by way of the first-high-frequency-electrode current supply line 162 and the second-high-frequency-electrode current supply line 262 passing through the cable 360. The power applied is, for example, in the range of 20 W to 80 W. As a result, the living tissue is heated and cauterized. The cauterized tissue undergoes a change in property and coagulates.

After stopping the output of the high-frequency energy, the control device 370 applies power to the electrothermal conversion element 130 so that the temperature of the first high-frequency electrode 110 becomes the target temperature. The target temperature is 200° C., for example. At the time, a current flows from the control device 370 to the electric resistance pattern 134 of the electrothermal conversion element 130 by way of the cable 360 and the first-heater current supply lines 164. The electric resistance pattern 134 generates heat when it is supplied with a current. The heat generated by the electric resistance pattern 134 is transferred to the first high-frequency electrode 110 through the high-thermal-conductivity heat-resistant adhesive sheet 120. As a result, the temperature of the first high-frequency electrode 110 increases.

Likewise, power is applied to the electrothermal conversion element 230 so that the temperature of the second high-frequency electrode 210 becomes a target temperature. The control device 370 applies power to the electrothermal conversion element 230 of the second electrode section 200 through the cable 360 and the second-heater current supply lines 264. As a result, the temperature of the second high-frequency electrode 210 increases.

Because of the heat mentioned above, the living tissue kept in contact with the first high-frequency electrode 110 or the second high-frequency electrode 210 is further cauterized and coagulated. After the living tissue is heated and coagulated, the output of the thermal energy is stopped. At the end, the operator operates the operation knob 352 to move the cutter 345 and cut off the living tissue. In this manner, the treatment of the living tissue is ended.

As described above, for example, the first high-frequency electrode 110 comes into contact with a living tissue at the first major surface, which is the opposite side of the second major surface, and serves as a heat conduction plate for transferring heat to the living tissue. For example, the substrate 132 is formed on the second major surface side of the heat conduction plate and comprises a projected portion projected from the heat conduction plate. For example, the electric resistance pattern 134 is thermally coupled to the heat conduction plate and serves as an electric resistance pattern which is formed on the substrate and which generates heat when applied with voltage. For example, the first lead connection portions 136 are formed on the projected portion of the substrate, and function as first lead connection portions electrically connected to the electric resistance pattern. For example, the first-heater current supply lines 164 are located closer to the heat conduction plate than is the substrate, are electrically connected to the first lead connection portions, and serve as first lead lines for applying power to the electric resistance pattern. For example, the second lead connection portion 138 is formed on the projected portion of the substrate, is electrically insulated from the first lead connection portions, and serves as second lead connection portions electrically connected to the heat conduction portion. For example, the first-high-frequency-electrode current supply line 162 is located closer to the heat conduction plate than is the substrate, is electrically connected to the second lead connection portion, and serves as second lead line for applying high-frequency voltage to the heat conduction plate. For example, the high-thermal-conductivity heat-resistant adhesive sheet 120 is located between the heat conduction plate and the electric resistance pattern, and serves as an adhesive sheet for thermal coupling between the electric resistance pattern and the heat conduction plate.

According to the present embodiment, the wiring line for applying power to the first high-frequency electrode 110 etc. are provided on the polyimide substrate 132 extended from the first high-frequency electrode 110. With this structure, the first electrode section 100 can be as thin as possible. The same holds true of the second electrode section 200 as well.

As a result, the holding section 320 of the energy treatment tool 310 can be small in size.

Second Embodiment

A description will now be given of the second embodiment. In the description below, reference will be made to how the second embodiment differs from the first embodiment. Those elements which are similar to the elements of the first embodiments will be denoted by the same reference numerals as used above, and a detailed description of such elements will be omitted. The second embodiment differs from the first embodiment in that the first electrode section 100 and the second electrode section 200 of the first embodiment are replaced with a heat conduction portion 600.

The heat conduction portion 600 of the second embodiment generates heat and heats a living tissue, but does not apply a high-frequency voltage to the living tissue. Part of the method for manufacturing the heat conduction portion 600 of the second embodiment is schematically shown in FIGS. 14A to 14D. Since the second embodiment does not apply a high-frequency voltage to a living tissue, the first high-frequency electrode 110 as used in the first embodiment is replaced with a heat conduction plate 610. The heat conduction plate 610 is made of a material having electric insulation property and being excellent in heat conduction property, such as a ceramic, alumina or aluminum nitride.

As shown in FIG. 14A, in the second embodiment, the high-thermal-conductivity heat-resistant adhesive sheet 120 and the electrothermal conversion element 130 of the first embodiment are replaced with an electrothermal conversion element 630. The electrothermal conversion element 630 includes an adhesive sheet 632 functioning as a substrate. An electric resistance pattern 634 and a lead connection portion 636 electrically connected to the electric resistance pattern 634 are formed on one of the surfaces of the adhesive sheet 632.

As shown in FIG. 14B, the electrothermal conversion element 630 is stacked on the heat conduction plate 610, with the surface on which the electric resistance pattern 634 is formed being in contact with the heat conduction plate 610. The electrothermal conversion element 630 and the heat conduction plate 610 are subjected to hot pressing, with a heavy weight applied. As a result, the electrothermal conversion element 630 and the heat conduction plate 610 are adhered to each other by the adhesive sheet 632, as shown in FIG. 14C. As in the first embodiment, a cover member is adhered, by use of a heat-resistant adhesive layer, to the surface of the adhesive sheet 632 on which the electric resistance pattern 634 is not formed. Then, as shown in FIG. 14D, a first-heater current supply line 164 is connected to the lead connection portion 636, and the connection portion is sealed with a sealer 670. The adhesive sheet 632 serves as an adhesive sheet for adhering the heat conduction plate and the electric resistance pattern.

Like the first embodiment, the second embodiment is advantageous in that the heat conduction portion 600 is as thin as possible, and the holding section 320 of the energy treatment tool 310 can be made small in size. In addition, since the second embodiment does not employ a high-thermal-conductivity heat-resistant adhesive sheet such as that used in the first embodiment, the second embodiment enables reduction of the number of parts required and reduction of the number of manufacturing steps required, as compared with the first embodiment. Furthermore, the reduction of the number of parts and the reduction of the number of manufacturing steps result in a low manufacturing cost.

If the second embodiment should be configured to apply a high-frequency voltage to a living tissue, as in the first embodiment, then the heat conduction portion 600 is replaced with an electrode made of e.g. copper, and an insulation film is provided between the electrode and the electric resistance pattern 634 etc. of the electrothermal conversion element 630.

Third Embodiment

A description will now be given of the third embodiment. In the description below, reference will be made to how the third embodiment differs from the first embodiment. Those elements which are similar to the elements of the first embodiments will be denoted by the same reference numerals as used above, and a detailed description of such elements will be omitted. The third embodiment differs from the first embodiment in that the first electrode section 100 and the second electrode section 200 of the first embodiment are replaced with a heat conduction portion 700.

Figure 15A:
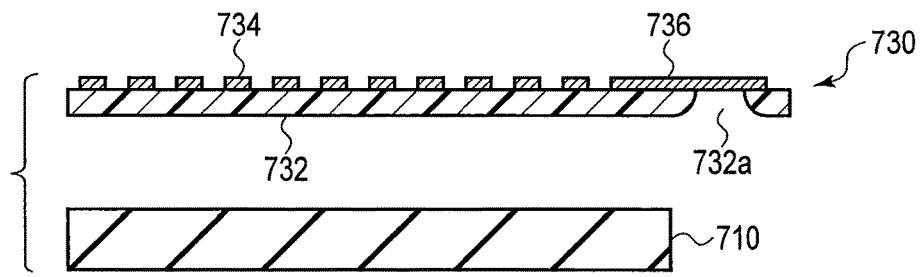
FIG. 15A is an explanatory view showing an example of a heat transfer member and an example of a manufacturing method according to the third embodiment.
Figure 15B:
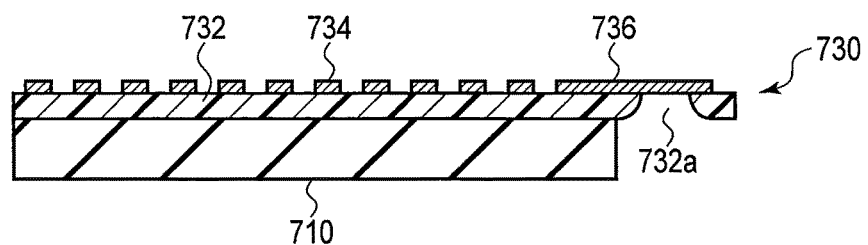
FIG. 15B is an explanatory view showing an example of a heat transfer member and an example of a manufacturing method according to the third embodiment.
Figure 15C:
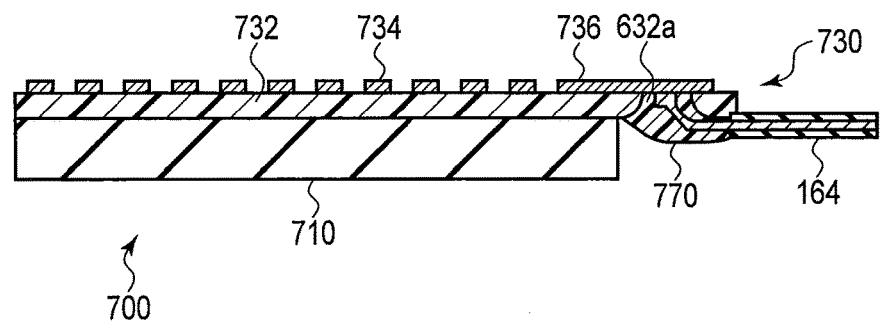
FIG. 15C is an explanatory view showing an example of a heat transfer member and an example of a manufacturing method according to the third embodiment.

The heat conduction portion 700 of the third embodiment generates heat and heats a living tissue but does not apply a high-frequency voltage to the living tissue. Part of the method for manufacturing the heat conduction portion 700 of the third embodiment is schematically shown in FIGS. 15A to 15C. Since the third embodiment does not apply a high-frequency voltage to a living tissue, the first high-frequency electrode 110 as used in the first embodiment is replaced with a heat conduction plate 710.

As shown in FIG. 15A, in the third embodiment, the high-thermal-conductivity heat-resistant adhesive sheet 120 and the electrothermal conversion element 130 of the first embodiment are replaced with an electrothermal conversion element 730. The electrothermal conversion element 730 includes an adhesive sheet 732 functioning as a substrate. Like the high-thermal-conductivity heat-resistant adhesive sheet 120 of the first embodiment, the adhesive sheet 732 is formed, for example, by mixing a ceramic material having high thermal conductivity with epoxy resin. The adhesive sheet 732 has high adhesive property, satisfactory thermal conductivity and electric insulation property. An electric resistance pattern 734 and a lead connection portion 736 electrically connected to the electric resistance pattern 734 are formed on one of the surfaces of the adhesive sheet 732. The adhesive sheet 732 has an opening 732a at the position where the lead connection portion 736 is formed.

As shown in FIG. 15B, the electrothermal conversion element 730 is stacked on the heat conduction plate 710, with the surface on which the electric resistance pattern 734 is not formed being in contact with the heat conduction plate 710. The electrothermal conversion element 730 and the heat conduction plate 710 are subjected to hot pressing, with a heavy weight applied, with the result that they are adhered to each other by the adhesive sheet 732. As in the first embodiment, a cover member is adhered, by use of a heat-resistant adhesive layer, to the surface on which the electric resistance pattern 734 is formed. Then, as shown in FIG. 15C, a first-heater current supply line 164 is connected to the lead connection portion 736 through the opening 732a, and the connection portion is sealed with a sealer 770. The adhesive sheet 732 serves as an adhesive sheet which is located between the heat conduction plate and the electric resistance pattern and which thermally couples the electric resistance pattern and the heat conduction plate.

Like the first embodiment, the third embodiment is advantageous in that the heat conduction portion 600 is as thin as possible, and the holding section 320 of the energy treatment tool 310 can be made small in size. In addition, since the third embodiment does not employ a high-thermal-conductivity heat-resistant adhesive sheet such as that used in the first embodiment, the third embodiment enables reduction of the number of parts required and reduction of the number of manufacturing steps required, as compared with the first embodiment. Furthermore, the reduction of the number of parts and the reduction of the number of manufacturing steps result in a low manufacturing cost.

The third embodiment differs from the second embodiment in that the electric resistance pattern 734, etc. are insulated from the heat conduction plate 710 by the adhesive sheet 732. Therefore, the third embodiment can be modified to apply a high-frequency voltage to a living tissue, as in the first embodiment, by forming the heat conduction plate 710 as a copper electrode. In this case, a high-frequency-electrode current supply line has to be connected to the heat conduction plate 710. The high-frequency-electrode current supply line may be connected directly to the heat conduction plate 710. Alternatively, a lead line connection portion to which the high-frequency-electrode current supply line can be connected may be provided on the surface of the adhesive sheet 732 on which the electric resistance pattern 734 etc. are formed, and the lead line connection portion may be connected to the heat conduction plate 710 through the opening 732a. Furthermore, a lead line connection portion to which the high-frequency-electrode current supply line can be connected may be provided on the surface of the adhesive sheet 732 on which the electric resistance pattern 734 etc.

are not formed, and the high-frequency-electrode power supply line and the heat conduction plate 710 may be connected through the lead line connection portion.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A therapeutic treatment device for treating a living tissue by heating, the therapeutic treatment device comprising:
    a heat conduction plate comprising a first major surface arranged on a first plane and a second major surface arranged on a second plane substantially parallel to the first plane,
        wherein the heat conduction plate extends along a longitudinal axis between a distal end and a proximal end, and
        wherein the proximal end comprises a proximal edge connecting the first major surface of the heat conduction plate and the second major surface of the heat conduction plate along an orthogonal axis orthogonal to the longitudinal axis;
    a substrate layer comprising a first major surface arranged on a third plane substantially parallel to the first plane and the second plane, and a second major surface arranged on a fourth plane substantially parallel to the first plane, the second plane and the third plane,
        wherein a first portion of the first major surface of the substrate layer faces the second major surface of the heat conduction plate, and
        wherein a second portion of the first major surface of the substrate layer and the proximal edge of the heat conduction plate define a space that is proximal of the proximal edge of the heat conduction plate along the longitudinal axis and extends along the orthogonal axis from the first major surface of the substrate layer to the first plane,
    an electric resistance pattern arranged on the first portion of the first major surface of the substrate layer between the second plane and the third plane;
    a first lead connection portion electrically connected to the electric resistance pattern, wherein at least a portion of the first lead connection portion is arranged on the second portion of the first major surface of the substrate layer and in the space; and
    a first lead line,
        wherein a connected portion of the first lead line is mechanically connected to the first lead connection portion to electrically connect the first lead line and the electric resistance pattern via the first lead connection portion to apply power to the electric resistance pattern to generate heat that is conducted from the second major surface of the heat conduction plate to the first major surface of the heat conduction plate, and
        wherein the connected portion of the first lead line is arranged in the space.

2. The therapeutic treatment device according to claim 1, further comprising:
    an adhesive layer configured to connect the electric resistance pattern to the second major surface of the heat conduction plate,
    wherein the adhesive layer comprises a material that conducts the heat generated by the electric resistance pattern to the second major surface of the heat conduction plate and electrically insulates the electric resistance pattern from the heat conduction plate.

3. The therapeutic treatment device according to claim 1, wherein the substrate layer comprises an adhesive sheet adhered to the heat conduction plate and the electric resistance pattern.

4. The therapeutic treatment device according to claim 2, wherein the adhesive layer comprises a mixture of resin and a ceramic material.

5. The therapeutic treatment device according to claim 1, wherein the heat conduction plate is electrically conductive, and
    wherein the therapeutic treatment device further comprises:
        a second lead connection portion electrically connected to the heat conduction plate and electrically insulated from the first lead connection portion, wherein at least a portion of the second lead connection portion is arranged on the second portion of the first major surface of the substrate layer and in the space; and
        a second lead line,
            wherein a connected portion of the second lead line is mechanically connected to the second lead connection portion to electrically connect the second lead line and the heat conduction plate, and
            wherein the connected portion of the second lead line is arranged in the space.

* * * * *